(12) United States Patent
Nakazawa et al.

(10) Patent No.: US 9,150,911 B2
(45) Date of Patent: Oct. 6, 2015

(54) NUCLEIC ACID ANALYSIS REACTION CELL AND NUCLEIC ACID ANALYZER

(75) Inventors: Taro Nakazawa, Hitachinaka (JP);
Masatoshi Narahara, Hitachinaka (JP);
Ryoji Inaba, Hitachinaka (JP);
Yoshihiro Nagaoka, Ushiku (JP);
Shigenori Togashi, Abiko (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 13/696,962

(22) PCT Filed: Apr. 20, 2011

(86) PCT No.: PCT/JP2011/002299
§ 371 (c)(1),
(2), (4) Date: Dec. 7, 2012

(87) PCT Pub. No.: WO2011/142085
PCT Pub. Date: Nov. 17, 2011

(65) Prior Publication Data
US 2013/0084629 A1 Apr. 4, 2013

(30) Foreign Application Priority Data
May 11, 2010 (JP) .................................. 2010-108898

(51) Int. Cl.
*C12Q 1/68* (2006.01)
*B01L 3/00* (2006.01)
(Continued)

(52) U.S. Cl.
CPC .......... *C12Q 1/6844* (2013.01); *B01L 3/502746* (2013.01); *G01N 27/447* (2013.01);
(Continued)

(58) Field of Classification Search
CPC ................ B01L 2300/0816; B01L 2300/0861; B01L 2300/0864; B01L 2300/0877; B01L 2300/0887; B01L 2400/086; B01L 3/502746; C12Q 1/6844; G01N 27/447; G01N 35/1095

USPC .......................... 435/283.1–309.4; 73/204.26
See application file for complete search history.

(56) References Cited

U.S. PATENT DOCUMENTS 6,432,630 B1* 8/2002 Blankenstein ................... 435/4
2003/0162283 A1 8/2003 Kuno et al.
(Continued)

FOREIGN PATENT DOCUMENTS

JP 2003-315337 A 11/2003
JP 2006-337245 A 12/2006
(Continued)

OTHER PUBLICATIONS

Marcel Margulies et al., "Genome Sequencing in Open Microfabricated High Density Picoliter Reactors", Nature, Sep. 15, 2005, pp. 376-380, vol. 437, No. 7057.
(Continued)

*Primary Examiner* — Nathan Bowers
*Assistant Examiner* — Lydia Edwards
(74) *Attorney, Agent, or Firm* — Crowell & Moring LLP

(57) ABSTRACT

A nucleic acid analysis reaction cell and a nucleic acid analyzer are provided, in which a uniform flow rate is realized, so that a portion where a flow rate is low is removed and washing time for reagent removal is shortened.
A flow path (103) is provided which includes a detection area (108) for detecting sequence information of a nucleic acid fragment and detection outer areas (107) disposed at both ends of the detection area (108). An inflow port (105) is provided in one of the detection outer areas (107) and a discharge port (106) is provided in the other of the detection outer areas (107). The detection outer areas (107) disposed at both the ends of the detection area (108) are areas whose widths become narrow toward ends, and guides (104) for branching a liquid are provided in at least the detection outer area (107) in which the inflow port (105) is provided.

3 Claims, 4 Drawing Sheets

(51) Int. Cl.
    *G01N 27/447*      (2006.01)
    *G01N 35/10*       (2006.01)
(52) U.S. Cl.
    CPC ..... *G01N35/1095* (2013.01); *B01L 2300/0816* (2013.01); *B01L 2300/0861* (2013.01); *B01L 2300/0864* (2013.01); *B01L 2300/0877* (2013.01); *B01L 2300/0887* (2013.01); *B01L 2400/086* (2013.01)

(56) References Cited

U.S. PATENT DOCUMENTS

| | | | | |
|---|---|---|---|---|
| 2005/0229696 | A1* | 10/2005 | Takayama | 73/204.26 |
| 2007/0004029 | A1 | 1/2007 | Aoyagi | |

FOREIGN PATENT DOCUMENTS

| | | | |
|---|---|---|---|
| JP | 2007-10325 | A | 1/2007 |
| JP | 2007-33090 | A | 2/2007 |
| JP | 2007-40969 | A | 2/2007 |
| JP | 2008-298598 | A | 12/2008 |
| JP | 2009-8690 | A | 1/2009 |
| JP | 2009-109232 | A | 5/2009 |
| JP | 2009-250872 | A | 10/2009 |
| JP | 2009-543054 | A | 12/2009 |
| WO | WO 2008/005166 | A2 | 1/2008 |

OTHER PUBLICATIONS

Jay Shendure et al., "Accurate Multiplex Polony Sequencing of an Evolved Bacterial Genome", Science, Sep. 9, 2005, pp. 1728-1732, vol. 309, www.sciencemag.org.
Timothy D. Harris et al., "Single-Molecule DNA Sequencing of a Viral Genome", Science, Apr. 4, 2008, pp. 106-109, vol. 320, www.sciencemag.com.
Jingyue Ju et al., "Four-color DNA sequencing by synthesis using cleavable fluorescent nucleotide reversible terminators", PNAS, Dec. 26, 2006, pp. 19635-19640, vol. 103, No. 52.
International Search Report dated Jun. 7, 2011 including English-language translation (Two (2) pages).
Japanese Office Action dated Jan. 8, 2013 (two (2) pages).
Japanese Office Action dated Oct. 2, 2012 (two (2) pages).

* cited by examiner

NUCLEIC ACID ANALYSIS REACTION CELL AND NUCLEIC ACID ANALYZER

TECHNICAL FIELD

The present invention relates to a nucleic acid analysis reaction cell and a nucleic acid analyser that are used when sequence information of a nucleic acid fragment is determined.

BACKGROUND ART

A new technology to determine base sequence of DNA or RNA is developed.

At present, in a normally used method of using electrophoresis, a cDNA fragment sample synthesized in advance through a reverse transcription reaction of a DNA fragment or RNA sample for sequencing is prepared, electrophoresis is performed after a dideoxy reaction by the well-known Sanger method is performed, and a molecular weight separation/expansion pattern is measured and analyzed.

On the other hand, in recent years, a method is proposed in which multiple DNA fragments as samples are fixed on a substrate, and sequence information of the multiple fragments is determined in parallel.

In Non Patent Literature 1, fine particles are used as vehicles for carrying DNA fragments, and PCR is performed on the fine particles. Thereafter, the fine particles carrying the PCR-amplified DNA fragments are placed on a plate provided with multiple holes each having a hole diameter corresponding to the size of the fine particle, and are read by a pyrosequence method.

In Non Patent Literature 2, fine particles are used as vehicles for carrying DNA fragments, and PCR is performed on the fine particles. Thereafter, the fine particles are dispersed on a glass substrate and are fixed, an enzyme reaction (ligation) is performed on the glass substrate, substrates with fluorescent dyes are captured and fluorescent detection is performed, so that sequence information of the respective fragments is obtained.

In Non Patent Literature 3, multiple DNA probes having the same sequence are fixed on a smooth substrate. Besides, after a DNA sample is cut, a DNA probe sequence and an adapter sequence of a complementary strand are added to ends of each of the DNA sample fragments. These are hybridised on the substrate, so that the sample DNA fragments are randomly fixed one molecule by one molecule on the substrate. In this case, a DNA extension reaction is performed on the substrate, and after substrates with fluorescent dyes are captured, washing of unreacted substrates and fluorescent detection are performed, and the sequence information of the sample DNA is obtained.

As described above, the method is developed in which multiple nucleic acid fragment samples are fixed on the smooth substrate, so that the sequence information of the multiple fragments is determined in parallel, and is being put to practical use.

As a nucleic acid analysis reaction cell used in these systems, it is desirable that a detection area where a sample DNA or a fine particle carrying a sample DNA is firmly fixed is wider. Besides, in order to reduce the amount of sample DNA necessary for the sequence reaction and the amount of reaction reagent, it is desirable that the volume in the flow cell is less. Further, in order to reduce a dead volume outside the detection area, an inflow port of a reagent is required to be narrowed.

Besides, a chemical reaction in these methods generally includes many steps using different reagents, and it is necessary to supply solutions containing the different reagents in the respective steps. A reagent used in a former step often becomes a reaction inhibition factor or a cause of erroneous detection in the next step, and it is necessary to perform a washing step between the steps and to completely remove the reagent used in the former step.

Patent Literature 1 discloses that a columnar member for reducing a cross section is provided in a portion where the width of a biochemical reaction cassette is wide.

CITATION LIST

Patent Literature

PTL 1: JP-A-2007-40969

Non Patent Literature

NPL 1: Nature 2005, Vol. 437, pp. 376-380
NPL 2: Science 2005, Vol. 309, pp. 1728-1732
NPL 3: Science 2008, Vol. 320, pp. 106-109
NPL 4: P.N.A.S. 2006, vol. 103, pp. 19635-19640

SUMMARY OF INVENTION

Technical Problem

However, in Patent Literature 1, before the solution reaches the columnar member, the flow rate becomes high at the center part and the flow rate becomes low at the end. Accordingly, there is a problem that it is difficult to realise a uniform flow rate. If there is a portion where the flow rate is low, washing time for reagent removal becomes long.

The invention solves the above problem, and an object thereof is to provide a nucleic acid analysis reaction cell and a nucleic acid analyzer in which a uniform flow rate is realized, so that a portion where a flow rate is low is removed, and washing time for reagent removal is shortened.

Solution to Problem

A nucleic acid analysis reaction cell of the invention includes a branch member on at least an inflow port side and in an area (detection outer area) where a width becomes narrow toward an end.

Advantageous Effects of Invention

The nucleic acid analysis reaction cell and the nucleic acid analyzer can be provided in which the uniform flow rate is realized by using the branch member, so that a portion where the flow rate is low is removed, and the washing time for reagent removal is shortened.

DESCRIPTION OF EMBODIMENTS

An embodiment of the invention will be described by use of FIG. 1. A nucleic acid analysis reaction cell of the invention is formed such that an inorganic or organic smooth plate 101 is bonded to an inorganic or organic smooth plate 102. Since the smooth plate 102 is provided with a groove as shown in FIG. 1, when the smooth plate 101 and the smooth plate 102 are bonded to each other, a flow path 103 is formed between both the plates.

Figure 1:
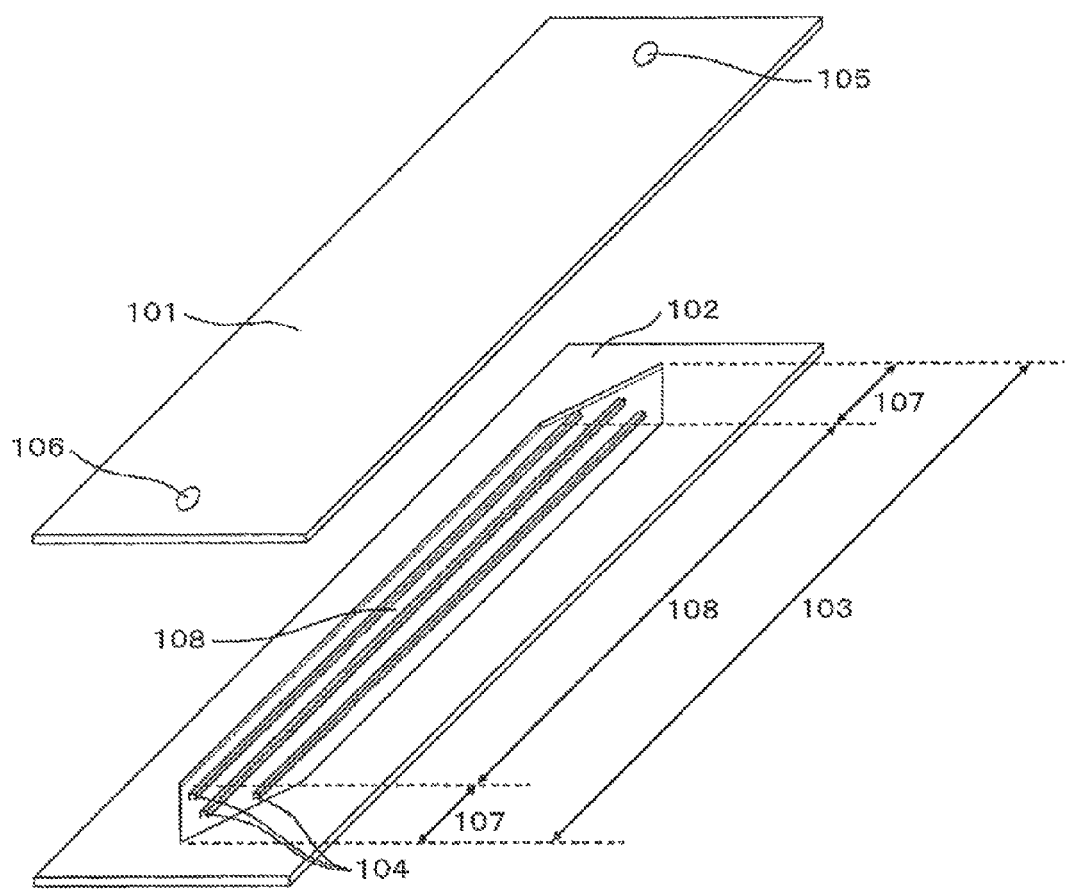
FIG. 1 A view for explaining an example of a structure of a nucleic acid analysis reaction cell of the invention.

FIG. 1 shows a perspective view of a state in which the smooth plate 101 and the smooth plate 102 are separated from each other. A plane shape of each of the smooth plates 101 and 102 is rectangular. The smooth plate 102 is provided with the groove having a uniform depth along a longitudinal direction, and the groove forms the flow path 103. The shape of each of both ends of the groove in the longitudinal direction is a taper shape in which the width becomes narrow toward the end.

An inorganic or organic guide (branch member) 104 stands in a portion of the flow path 103 of the smooth plate 102, and is joined to the smooth plate 101 and the smooth plate 102. That is, the guide 104 preferably has such a height that it reaches the smooth plate 101 when the smooth plate 101 and the smooth plate 102 are bonded to each other. The guide 104 extends along the longitudinal direction of the flow path 103. Besides, a plurality of the guides 104 are provided at almost equal intervals in a direction perpendicular to the longitudinal direction of the flow path 103.

An inflow port 105 and a discharge port (outflow port) 106 face the flow path 103, and various samples and reagents are injected and discharged from here.

Either one of the smooth plate 101 and the smooth plate 102 is inevitably transparent in order to perform optical detection and analysis. For example, in a verification experiment described below, glass is used for the smooth plate 101, and a silicon wafer which is subjected to plasma etching and in which the flow path 103 and the guides 104 are formed is used for the smooth plate 102. In addition, for example, thermoplastic resin such as polyethylene (PE), polypropylene (PP), polyvinyl chloride (PVC), acrylic resin (PMMA) or polydimethylsiloxane (PDMS), or thermosetting resin such as epoxy resin (EP) or unsaturated polyester resin (UP) is conceivable.

With respect to the bonding method of the smooth plate 101 and the smooth plate 102, in addition to anodic bonding, for example, welding or adhesion is conceivable. As the welding, heat welding, vibration welding, ultrasonic welding, laser welding and the like are enumerated as examples. Besides, as the adhesion, chemical adhesion using ionic bond, covalent bond or hydrogen bond, dispersive adhesion using Van der Waals force, electrostatic adhesion using electrostatic force, diffusion adhesion typified by dissolution or sintering, and the like are enumerated as examples.

The flow path 103 is divided into a detection area 108 in which the width is uniform in the direction perpendicular to the longitudinal direction, and a taper-shaped detection outer area 107 in which the width becomes narrow toward the end in the longitudinal direction. Although DNA to be measured or an immobilisation layer for immobilizing DNA to be measured is provided on one surface of the detection area 108, this shall not apply to the detection outer area 107 as far as the objective function is obtained.

Although FIG. 2 to FIG. 5 specifically show shapes of the guide 104 of the invention, the invention is not naturally limited to these shapes.

Figure 2:
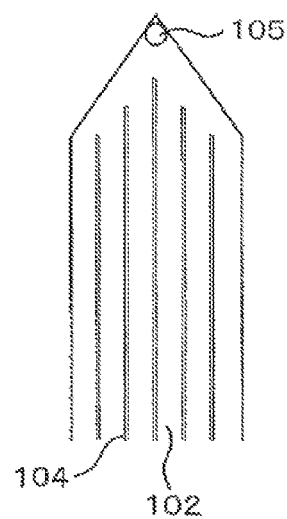
FIG. 2 A view showing a vicinity of an inflow port of a nucleic acid analysis reaction cell of the invention, FIG. 3 A view for explaining an example of the invention different from FIG. 2 and showing a vicinity of an inflow port of a nucleic acid analysis reaction cell.
Figure 3:
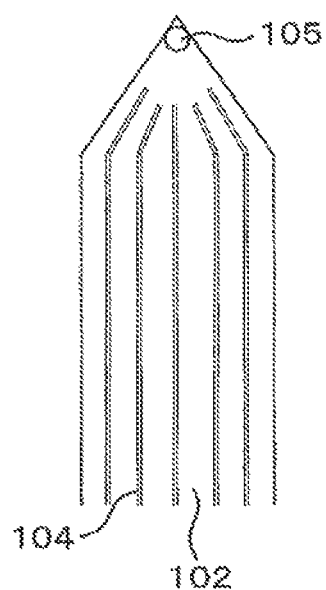

FIG. 2 shows one of preferable examples in the configuration of the guide 104 of the invention. FIG. 2 shows one of configurations in which the guides are formed so that distances between the guides 104 are kept more uniform, and the flow rate in each flow path becomes uniform. A fluid flowing into the flow path 103 from the inflow port 105 is divided by the guides 104. Here, an important point is that the guides 104 are provided in the detection outer area. FIG. 3 shows a modified example of FIG. 2, in which the guides 104 are provided along the outer periphery of the flow path. That is, the guides 104 in the detection outer area are formed so as to have the same shape as the taper-shaped flow path. In the shape typified in FIG. 2 and FIG. 3, the guides 104 are formed in the detection area 108 and the detection outer area 107, and by this, the flow rate can be made uniform, and as compared with the configuration of FIG. 4 and FIG. 5 described next, an effect of reducing distortion of the nucleic acid analysis reaction cell is high.

Figure 4:
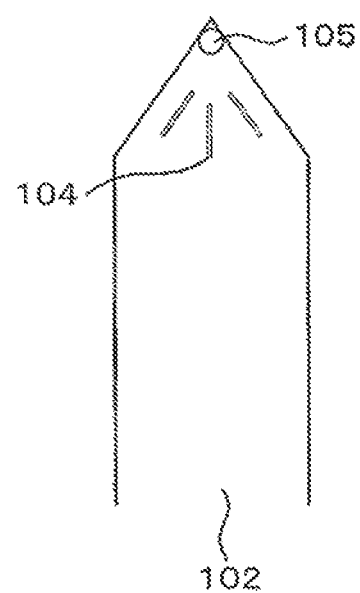
FIG. 4 A view for explaining an example of the invention different from FIG. 2 and FIG. 3 and showing a vicinity of an inflow port of a nucleic acid analysis reaction cell.

FIG. 4 shows one of other examples of the invention in which the guides 104 are formed only in the detection outer area and are not formed in the detection area. If the guides 104 exist in the detection area, the detection area is narrowed by the guides 104. Then, as shown in FIG. 4, the guides 104 are disposed only in the detection outer area, so that the throughput of analysis can not be increased.

Figure 5:
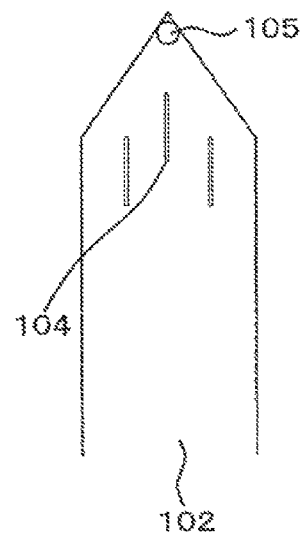
FIG. 5 A view for explaining an example of the invention different from FIG. 2 to FIG. 4 and showing a vicinity of an inflow port of a nucleic acid analysis reaction cell.

FIG. 5 shows an example in which the guides 104 are formed in the detection outer area and a partial area in the detection area. According to this example, distortion of a nucleic acid analysis substrate can be more reduced than the structure of FIG. 4, and the detection area can foe made larger than that of the structures of FIG. 2 and FIG. 3.

Incidentally, in the nucleic acid analysis reaction cell shown in FIG. 1 to FIG. 5, glass is used for the smooth plate 101, silicone is used for the smooth plate 102, and the plates are bonded by anodic bonding.

By using the nucleic acid analysis reaction cell as shown in FIG. 1 to FIG. 5, the flow rate in the flow path can be made uniform between the end part and the center part. That is, a portion where the flow rate is low can be removed, and washing time for reagent removal can be shortened. Especially, the flow rate must be made uniform in the taper-shaped portion, and in this embodiment, the guides are provided in the detection outer area. Further, in other words, if the guides are provided only in the detection area, the flow rate which has become irregular in the detection outer area is merely branched, and one of the objects of this application that the flow rate is made constant can not be achieved.

According to this embodiment, since the flow rate becomes uniform in the outside of the detection area, a portion where the flow rate is low can be removed, and washing time for reagent removal can be shortened. Further, the structure was found in which the required amount of samples for bubble removal and the amount of reagent could be reduced and the distortion of the upper surface and the lower surface of the fluid, channel could be reduced, and the invention was completed.

In other words, the nucleic acid analysis reaction, cell of the invention includes a solid base member having a flow cell for forming one or plural flow channels, a liquid supply unit for supplying liquid to the flow cell, an irradiation light source and a detection unit, and the guides for branching the liquid are provided in the fluid channel. By this, the flow of the fluid from the inflow port for injecting the fluid to the fluid channel is controlled, and the flow rate in the outer peripheral part of the fluid channel can be raised. Thus, washing time for reagent removal is shortened, and further, the required amount of samples for bubble removal, the amount of reagent, and bubble removal time can also be reduced.

Besides, at least one surface of the solid base member constituting the flow cell is transparent, and DNA to be measured or the immobilisation layer for immobilising DNA to be measured exists on only one surface of the solid base member, which contacts the fluid channel. By this, DNA to be measured can be immobilised only on one surface in the fluid channel. Thus, the reagent required for the analysis and the DNA amount can be reduced.

Besides, the guides are joined to the upper surface and the lower surface of the fluid channel. By this, the distortion of the upper surface and the lower surface of the fluid channel can be reduced. Thus, the contact between the upper surface and the lower surface is suppressed, and a change in fluid channel inside volume due to distortion, a reduction in detection rate due to focus shift, a reduction in temperature adjustment rate due to defective contact to a temperature controlling unit and the like can be reduced.

Further, since it is generally desirable that a detection area in a flow cell is made wider and the amount of reaction reagent is made less, there is a tendency that the width of the flow path becomes wide and the height of the flow path becomes narrow. As a result, the ratio of the flow path width to the flow path height becomes large, and by this, the upper surface and the lower surface of the fluid channel are distorted according to the material of the flow path, and there is a structural problem that these contact each other. In JP-A-2007-40969, there is a problem that the distortion of the upper and lower surfaces in the flow path can not be solved structurally, and the trouble of the contact is accelerated.

Besides, according to the material of the flow path, when the fluid flows to the fluid channel, the fluid pushes up the upper surface and the lower surface of the fluid channel from the inside, so that the upper and the lower surfaces of the fluid channel are distorted, and there are such structural problems that the volume of the inside of the fluid channel is changed, the focus of the detection unit is not determined and the detection rate is reduced, and the flow cell can not closely contact the temperature controlling unit and the temperature adjustment rate is reduced.

According to the embodiment, washing time for reagent removal is reduced, the required amount of samples for bubble removal and the amount of reagent are reduced so that the throughput of the analysis is raised, and further, contact between the upper and lower surfaces of the fluid channel, reduction in detection rate and temperature control rate, and the like can be reduced.

Figure 6:
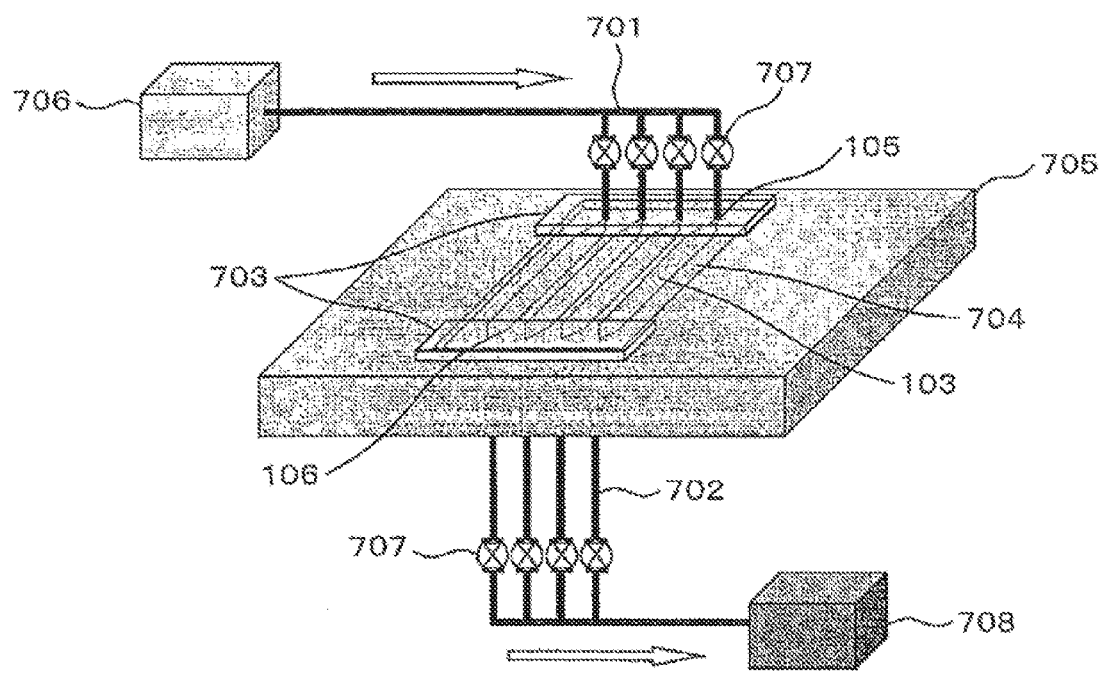
FIG. 6 A view showing a nucleic acid analysis flow cell in which the nucleic acid analysis reaction cell of the invention is mounted.

An example of a preferable structure of a nucleic acid analysis flow cell, will be described with reference to FIG. 6. A reaction chamber 704 in which plural flow paths 103 are mounted is placed on a temperature controlling unit 705. Arrangement intervals between the flow paths 103 can be appropriately set according to a nucleic acid sample to be analysed and the specification of a fluorescent detection apparatus. As shown in FIG. 6, the reaction chamber 704 is placed on the temperature controlling unit 705, is fixed by a clamp 703, and is used under a condition that liquid sending can be performed.

Specifically, these are constructed of the temperature controlling unit 705 to perform storage and temperature management of a nucleic acid sample, a reaction enzyme, a buffer, a nucleotide substrate and the like, a dispensing unit 706 to deliver a reaction liquid, valves 707 to control the flow of liquid for the respective flow paths 103, and a waste liquid tank 70S. The valves 707 are provided for the respective flow paths 103 and on the upstream side and the downstream side of the flow paths. As the need arises, a temperature controlling machine is disposed, and temperature control is performed. At the time of termination of the reaction, a washing liquid is supplied through the flow paths 103 and is stored in the waste liquid, tank 708. Injection nozzles 701 are connected between the dispensing unit 706 and the flow paths 103, and waste liquid hoses 702 are connected, between the flow paths 103 and the waste liquid tank 708.

Figure 7:
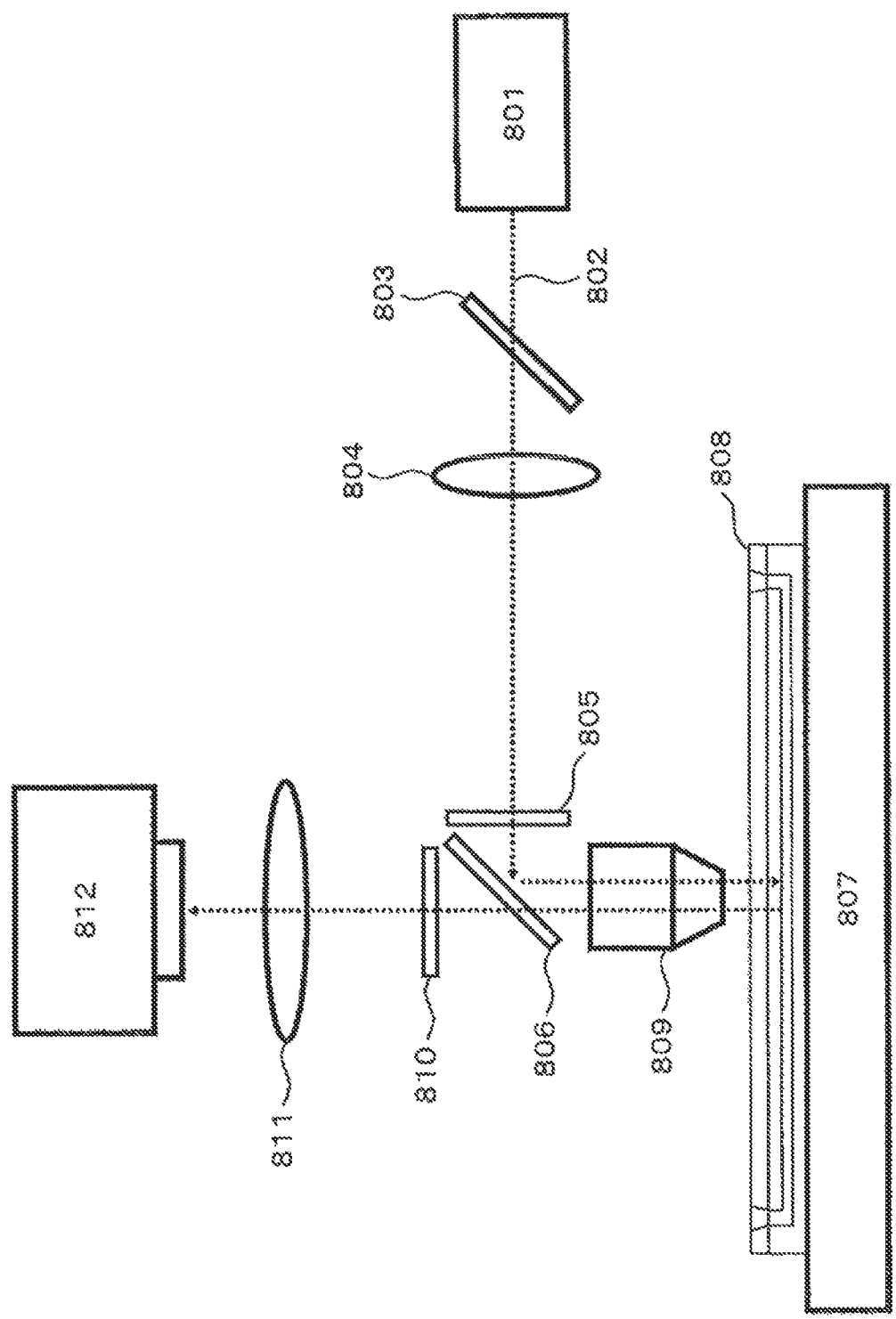
FIG. 7 A view showing a nucleic acid analyser in which an optical system and the like are disposed in a nucleic acid analysis flow cell of the invention.

A preferable structure of a nucleic acid analyzer will be described by use of FIG. 7. In this embodiment, there are provided means for supplying at lease one kind of biomolecules comprising a nucleotide, a nucleotide comprising a fluorescent dye, a nucleic acid synthetase, a primer and a nucleic acid sample to the nucleic acid analysis reaction cell, means for irradiating light to the nucleic acid analysis reaction cell, and fluorescence detection means for measuring the fluorescence of a fluorescent dye that is incorporated into a nucleic acid strand due to a nucleic acid extension reaction that occurs by way of the coexistence of the nucleotide, the nucleic acid synthetase and the nucleic acid sample on the nucleic acid analysis reaction cell. More specifically, a laser light 802 emitted from a Xe lamp module 801 passes through a cold mirror 803, a condenser lens 804 and an excitation filter 805, and is reflected by a dichroic mirror 806. After being reflected, the light impinges on a flow path in a nucleic acid reaction device 808 positioned on a stage 807, and causes a fluorescent material to emit light. The emitted light passes through an objective lens 809, passes through a light-emitting filter 810 and a tube lens 811, and is received by a CCD camera 812.

In the case of a successive reaction scheme, as a nucleotide with fluorescent dye, as disclosed in Non Patent Literature 4, one in which a 3'-O-allyl group is incorporated at the 3'OH position on a ribose as a protective group, and in which a fluorescent dye is linked to the 5-position of the pyrrolidines or the 7-position of the purines via an allyl group can be used. Since the allyl group is cleaved by illumination or through contact with palladium, it is possible to simultaneously attain dye quenching and control of the extension reaction. Even in the successive reaction, there is no need to remove unreached nucleotides by washing.

It would be easily understood for one of ordinary skill in the art that the invention is not limited to the foregoing embodiments, and can be variously modified within the scope of the invention set forth in the claims.

REFERENCE SIGNS LIST 101, 102 smooth plate
103 flow path
104 guide
105 inflow port
106 discharge port
701 injection nozzle
702 waste liquid hose
703 clamp 704 reaction chamber
705 temperature controlling unit
706 dispensing unit
707 valve
708 waste liquid tank
801 Xa lamp module
802 laser light
803 cold mirror
804 condenser lens
805 excitation filter
806 dichroic mirror
807 stage
608 nucleic acid reaction device
809 objective lens
810 light-emitting filter
811 tube lens
812 CCD camera

The invention claimed is:

1. A nucleic acid analysis reaction cell comprising:
a flow path including a detection area for detecting sequence information of a nucleic acid fragment and detection outer areas disposed at both ends of the detection area, and
substrates that are bonded to each other, wherein
an inflow port is provided in one of the detection outer areas and an outflow port is provided in the other of the detection outer areas,
the detection outer areas disposed at both the ends of the detection area are areas whose widths become narrow toward any end thereof, and
guides that are provided only in the detection outer area in which the inflow port is provided, wherein
each guide is configured to guide liquid along a predefined path within the detection outer area in which the inflow port is provided,
a flow rate of the liquid in each guide is substantially the same,
the guides are provided at equal intervals in a direction perpendicular to a longitudinal direction of the flow path,
a fluid flowing into the flow path from the inflow port is divided by the guides,
the number of the inflow port is one, and
each of the guides is joined to an upper surface and a lower surface of the flow path.

2. A nucleic acid analyzer comprising:
a nucleic acid analysis reaction cell that includes a flow path including a detection area for detecting sequence information of a nucleic acid fragment and detection outer areas disposed at both ends of the detection area;
a liquid supply unit for supplying a liquid;
substrates that are bonded to each other;
an irradiation light source; and
a detection unit, wherein
the flow path includes the detection area for detecting the sequence information of the nucleic acid fragment and the detection outer areas disposed at both the ends of the detection area,
an outflow port is provided in one of the detection outer areas and an inflow port is provided in the other of the detection outer areas,
the detection outer areas disposed at both the ends of the detection area are areas whose widths become narrow toward any end thereof, and
guides that are provided only in the detection outer area in which the inflow port is provided, wherein
each guide is configured to guide liquid along a predefined path within the detection outer area in which the inflow port is provided,
a flow rate of the liquid in each guide is substantially the same,
the guides are provided at equal intervals in a direction perpendicular to a longitudinal direction of the flow path,
a fluid flowing into the flow path from the inflow port is divided by the guides,
the number of the inflow port is one, and
each of the guides is joined to an upper surface and a lower surface of the flow path.

3. A nucleic acid analyzer comprising:
a nucleic acid analysis reaction cell that includes a flow path including a detection area for detecting sequence information of a nucleic acid fragment and detection outer areas disposed at both ends of the detection area;
a liquid supply unit for supplying a liquid;
substrates that are bonded to each other;
an irradiation light source; and
a detection unit, wherein
the flow path includes an immobilization layer immobilizing nucleic acid to be measured,
the immobilization layer is provided in the detection areas and the detection outer areas,
an inflow port is provided in one of the detection outer areas and an outflow port is provided in the other of the detection outer areas,
the width of the detection area is uniform in a direction perpendicular to a longitudinal direction,
the detection outer areas disposed at both ends of the detection area are areas whose widths become narrower toward any end thereof,
guides are provided only in the detection outer area in which the inflow port is provided,
each guide is configured to guide liquid along a predefined path within the detection outer area in which the inflow port is provided,
a flow rate of the liquid in each guide is substantially the same,
the guides are disposed at equal intervals in a direction perpendicular to a direction extending from the inflow port to the outflow port,
the guides are provided at equal intervals in a direction perpendicular to a longitudinal direction of the flow path,
a fluid flowing into the flow path from the inflow port is divided by the guides,
the number of the inflow port is one, and
each of the guides is joined to an upper surface and a lower surface of the flow path.

* * * * *